United States Patent
Williams et al.

(10) Patent No.: US 10,307,583 B2
(45) Date of Patent: Jun. 4, 2019

(54) ASEPTIC COUPLING DEVICES

(71) Applicant: Colder Products Company, St. Paul, MN (US)

(72) Inventors: Randall Williams, Minneapolis, MN (US); Loi Truong, Savage, MN (US); Blair Plackner, Pine Island, MN (US); Jeremy Henry Nichols, Maple Grove, MN (US)

(73) Assignee: Colder Products Company, St. Paul, MN (US)

( * ) Notice: Subject to any disclaimer, the term of this patent is extended or adjusted under 35 U.S.C. 154(b) by 459 days.

(21) Appl. No.: 15/144,380

(22) Filed: May 2, 2016

(65) Prior Publication Data

US 2016/0243348 A1    Aug. 25, 2016

Related U.S. Application Data

(62) Division of application No. 13/800,630, filed on Mar. 13, 2013, now Pat. No. 9,364,653.

(Continued)

(51) Int. Cl.
*F16L 37/30* (2006.01)
*A61M 39/18* (2006.01)
(Continued)

(52) U.S. Cl.
CPC ............ *A61M 39/18* (2013.01); *A61M 39/10* (2013.01); *A61M 39/165* (2013.01);
(Continued)

(58) Field of Classification Search
None
See application file for complete search history.

(56) References Cited

U.S. PATENT DOCUMENTS 3,391,951 A    7/1968    Miller
3,466,065 A    9/1969    Acker
(Continued)

FOREIGN PATENT DOCUMENTS

CN    101132828        2/2008
CN    102405369        4/2012
WO    2010118099 A2    10/2010

OTHER PUBLICATIONS

International Search Report and Written Opinion in PCT/US2013/031418 dated May 23, 2013, 9 pages.

(Continued)

*Primary Examiner* — Aaron M Dunwoody
*Assistant Examiner* — Fannie C Kee
(74) *Attorney, Agent, or Firm* — Fish & Richardson P.C.

(57) ABSTRACT

An aseptic coupling arrangement includes a first coupling device and a second aseptic coupling device. In one example, the first and second coupling devices are substantially similar, each having a main body having a front face and a fluid passageway therethrough. A first connecting feature on the main body of each coupling device may be provided for aligning and coupling the aseptic devices together. Each coupling device may also include a sealing member received in the main body and a membrane removably coupled to the main body front face to cover the sealing member. The first aseptic coupling device may also include a rotatable protective cover that is removably attached to the main body and connected to the membrane. In one example, the removal of the protective covers away from two coupled main bodies, in a direction parallel to the front faces, causes removal of the membranes.

22 Claims, 21 Drawing Sheets

Related U.S. Application Data

(60) Provisional application No. 61/639,121, filed on Apr. 27, 2012.

(51) Int. Cl.
*A61M 39/16* (2006.01)
*F16L 37/098* (2006.01)
*A61M 39/10* (2006.01)

(52) U.S. Cl.
CPC .......... *F16L 37/098* (2013.01); *F16L 37/30* (2013.01); *F16L 2201/10* (2013.01); *F16L 2201/44* (2013.01); *F16L 2201/80* (2013.01)

(56) References Cited

U.S. PATENT DOCUMENTS

| | | |
|---|---|---|
| 3,865,411 A | 2/1975 | Rowe et al. |
| 3,909,910 A | 10/1975 | Rowe |
| 4,019,512 A | 4/1977 | Tenczar |
| 4,022,205 A | 5/1977 | Tenczar |
| 4,030,494 A | 6/1977 | Tenczar |
| 6,655,655 B1 * | 12/2003 | Matkovich ......... A61M 39/1011 251/149.1 |
| 7,252,308 B2 | 8/2007 | Thilly |
| 2003/0030272 A1 | 2/2003 | Johnson et al. |
| 2009/0050213 A1 * | 2/2009 | Biddell .............. A61M 39/1011 137/15.01 |
| 2010/0230950 A1 | 9/2010 | Williams et al. |

OTHER PUBLICATIONS

International Report on Patentability in International application No. PCT/US2013/031418 dated Oct. 28, 2014, 5 pages.

\* cited by examiner

FIG. 18
FIG. 19
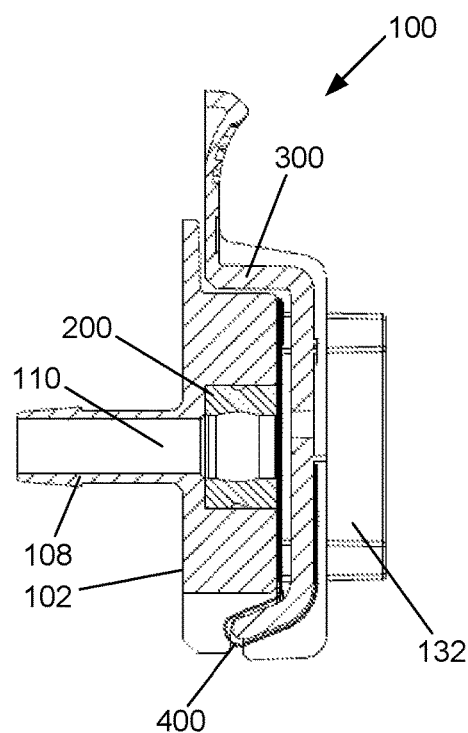
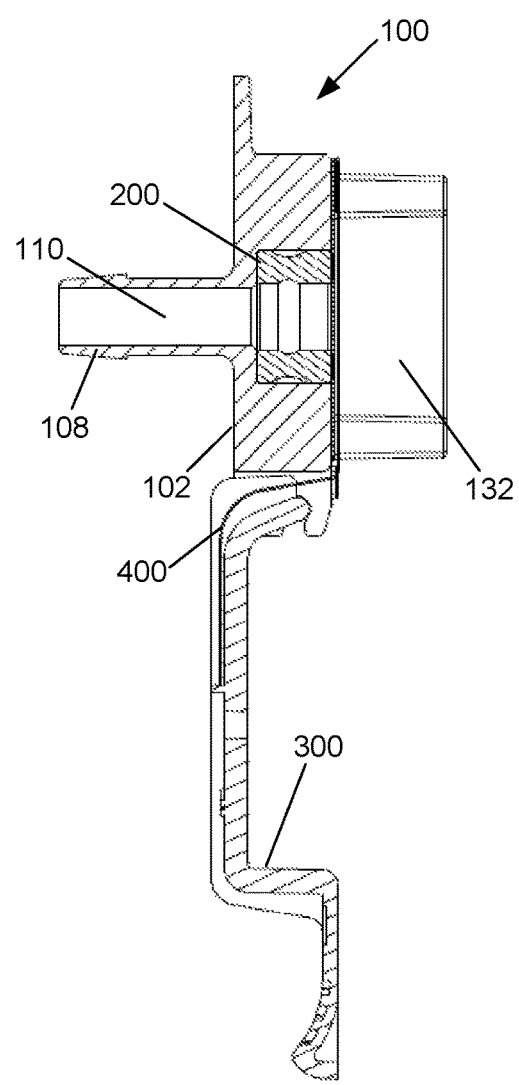

ASEPTIC COUPLING DEVICES

CROSS REFERENCE TO RELATED APPLICATION

This application is a divisional of application Ser. No. 13/800,630, filed Mar. 13, 2013, and titled "Aseptic Coupling Devices," which claims benefit to Application No. 61/639,121 filed Apr. 27, 2012, and titled "Aseptic Coupling Devices", the disclosure of which is hereby incorporated herein by reference.

BACKGROUND

Aseptic coupling devices can be used to connect two or more sterilized fluid pathways. For example, aseptic coupling devices can be used to couple a fluid pathway from a first piece of processing equipment or container to a fluid pathway from a second piece of processing equipment or container to establish a sterile pathway for fluid transfer therebetween. Typical aseptic coupling devices require a "dry-to-dry" or "dry connection" that is created using one or more pathway clamping devices placed upstream of the aseptic coupling devices so that the aseptic coupling devices are kept free of fluid while the connection between the aseptic coupling devices is made. Once the sterile connection between the aseptic coupling devices is made, the clamping devices are removed to allow fluid to flow through the aseptic coupling devices.

SUMMARY

This disclosure relates to aseptic coupling devices and arrangements. In accordance with the disclosure, a first aseptic coupling device for coupling to a second aseptic coupling device is disclosed. In one embodiment, the first aseptic coupling device has a first main body defining a front face and a first fluid passage therethrough. A first connecting feature disposed on the main body may be provided that is configured to couple the first aseptic device to the second aseptic coupling device. The first aseptic coupling device may also include a first sealing member received at least partially within the first main body, and a first membrane removably coupled to the front face of the first main body to cover the first sealing member.

The first aseptic coupling device may also include a first protective cover removably connected to the main body and connected to the first membrane. The first protective cover may be configured to be rotatable from a closed position, in which the protective cover covers at least a portion of the membrane covering the main body front face, to an open position in which the membrane covering the front face of the main body is exposed. In one embodiment, the removal of the first protective cover away from the main body in a direction parallel to the front face causes the first membrane to be removed from the front face.

An aseptic coupling arrangement is also disclosed that includes both the first and second aseptic coupling device, wherein the second aseptic coupling device has the same features as previously described for the first aseptic coupling device. For example, the second aseptic coupling device may include a second main body, a second connecting feature, a second sealing member, a second membrane, and a second protective cover. In one embodiment, the protective covers of each device are configured to be attached to each other such that the membranes of the first and second aseptic coupling devices can be removed from their respective front faces at the same time in simultaneous or near simultaneous fashion.

In one embodiment, the first and second connecting features each include a first connector and a second connector, wherein the second connector of the first aseptic coupling device can be received within the first connector of the second aseptic coupling device, and wherein the second connector of the second aseptic coupling device can be received within the first connector of the first aseptic coupling device. In one embodiment, the first and second connecting members of the first and second aseptic coupling devices are configured to align the front faces of each main body such that the front faces are parallel to each other. In one embodiment, the first and second aseptic coupling devices have a substantially similar construction.

A method for forming a sterile connection is also disclosed. One step includes providing first and second aseptic coupling devices wherein the first aseptic coupling device has a construction that is substantially similar to the second aseptic coupling device. The method may also include the steps of rotating a protective cover of the first aseptic coupling device to an open position to expose a membrane covering a front face of the first aseptic coupling device and rotating a protective cover of the second aseptic coupling device to an open position to expose a membrane covering a front face of the second aseptic coupling device. Additional steps in the method are connecting the first aseptic coupling device to the second aseptic coupling device and connecting the protective cover of the first aseptic coupling device to the protective cover of the second aseptic coupling device. A final step in the method may be removing membranes from the front faces of the first and second coupling devices by detaching the connected protective covers from the first and second coupling devices in a direction parallel to the front faces of each main body. Once the membranes have been removed in this fashion, a sterile fluid passageway through the first and second coupling devices is provided.

DESCRIPTION OF THE DRAWINGS

Non-limiting and non-exhaustive embodiments are described with reference to the following figures, which are not necessarily drawn to scale, wherein like reference numerals refer to like parts throughout the various views unless otherwise specified.

FIG. 18 is a first side cross-sectional view of the main body and protective cover of the coupling device of FIG. 7, with the protective cover being in a closed position.

FIG. 19 is a first side cross-sectional view of the main body and protective cover of the coupling device of FIG. 7, with the protective cover being in an open position.

DETAILED DESCRIPTION

Figure 1:
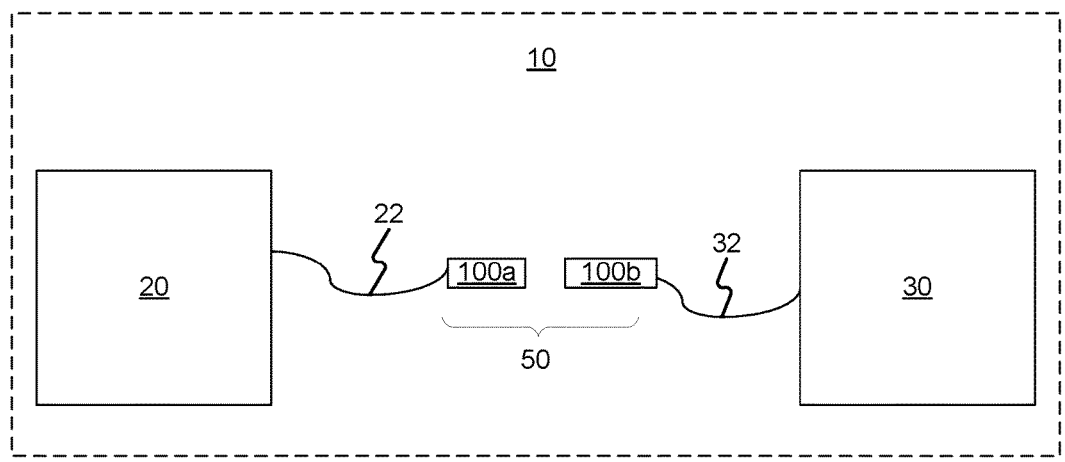
FIG. 1 is a schematic view of an example system including first and second pieces of processing equipment and an aseptic coupling device forming a sterile connection therebetween.

Various embodiments will be described in detail with reference to the drawings, wherein like reference numerals represent like parts and assemblies throughout the several views. Reference to various embodiments does not limit the scope of the claims attached hereto. Additionally, any examples set forth in this specification are not intended to be limiting and merely set forth some of the many possible embodiments for the appended claims.

As used herein, the term "sterilize" means a process of freeing, to a specified degree, a surface or volume from microorganisms. In example embodiments, the sterility of various components can be achieved using one or more sterilization techniques, including gamma irradiation, E-beam, ethylene oxide (EtO), and/or autoclave technologies.

As used herein, the term "aseptic" refers to any process that maintains a sterilized surface or volume.

As used herein, the term "fluid" means any substance that can be made to flow including, but not limited to, liquids, gases, granular or powdered solids, mixtures or emulsions of two or more fluids, suspensions of solids within liquids or gases, etc.

Referring now to FIG. 1, an example system 10 is shown. System 10 includes a first piece of processing equipment 20 and a second piece of processing equipment 30. In example embodiments, equipment 20 and 30 are bioreactors including biomaterial. In other embodiments, equipment 20 and 30 can be other apparatuses that require a sterile connection therebetween such as, for example, a bioreactor and a media bag or other receptacle.

Equipment 20 includes a fluid pathway 22 extending therefrom that is terminated by an aseptic coupling arrangement 50 including a first aseptic coupling device 100a. Likewise, equipment 30 includes a fluid pathway 32 extending therefrom that is terminated by a second aseptic coupling device 100b of the aseptic coupling arrangement 50. In example embodiments, aseptic coupling devices 100a and 100b are substantially similar (e.g., identical except for possibly differences in terminations). In example embodiments, the environment within pathways 22 and 32 and aseptic coupling devices 100a and 100a are sterile.

Figure 2:
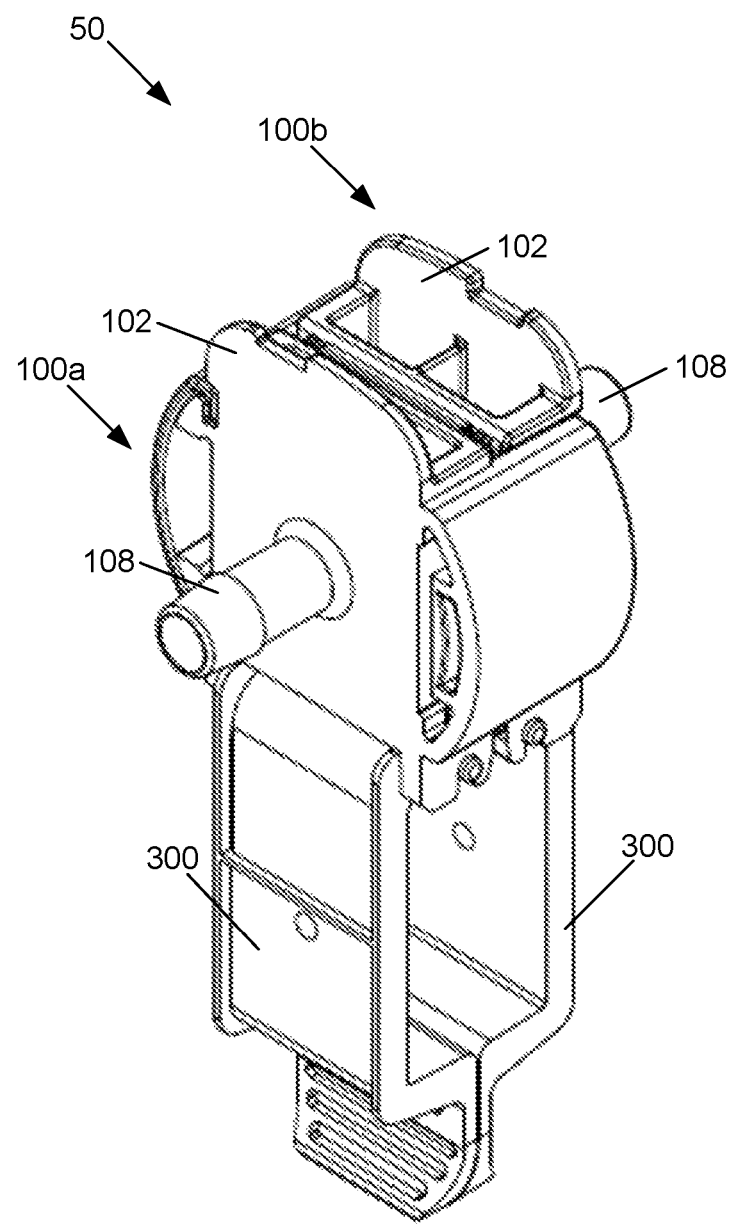
FIG. 2 is a perspective view of an example aseptic coupling arrangement in a pre-coupled state.
Figure 3:
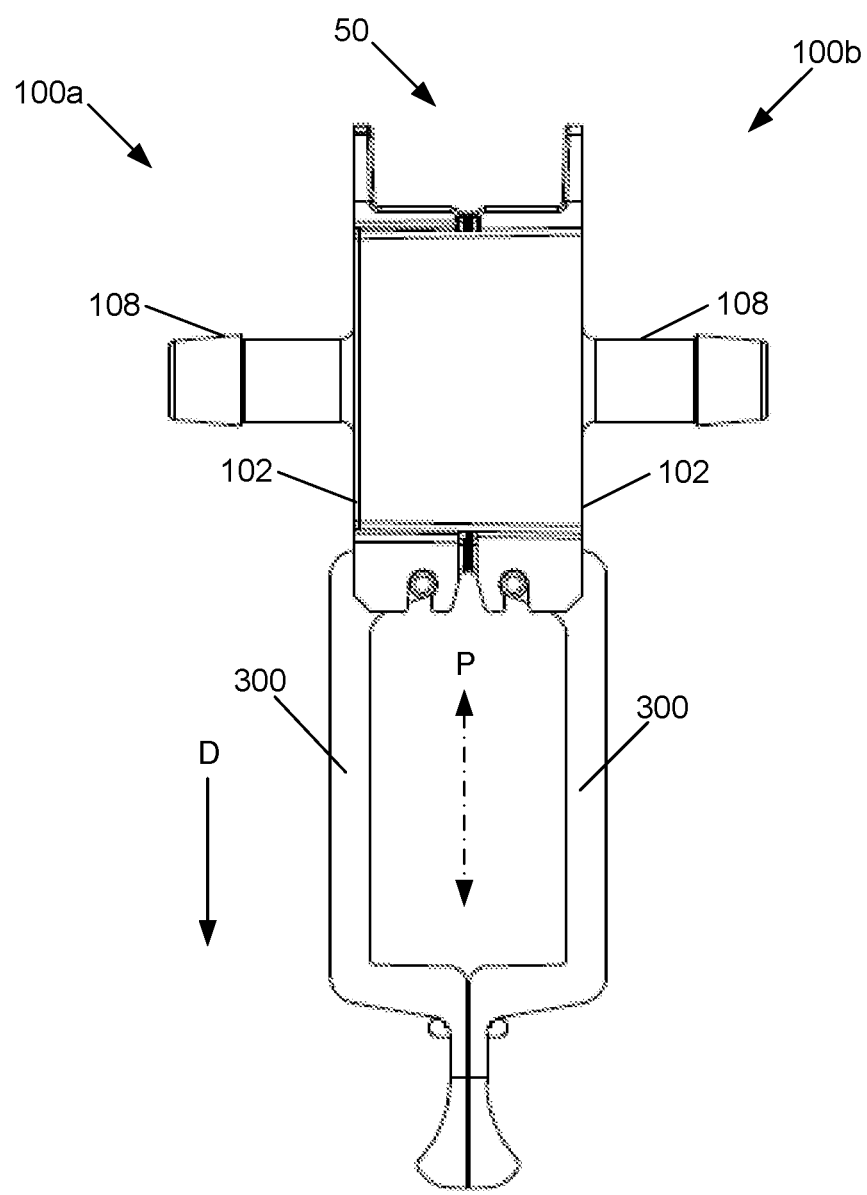
FIG. 3 is a side view of the aseptic coupling arrangement of FIG. 2.
Figure 4:
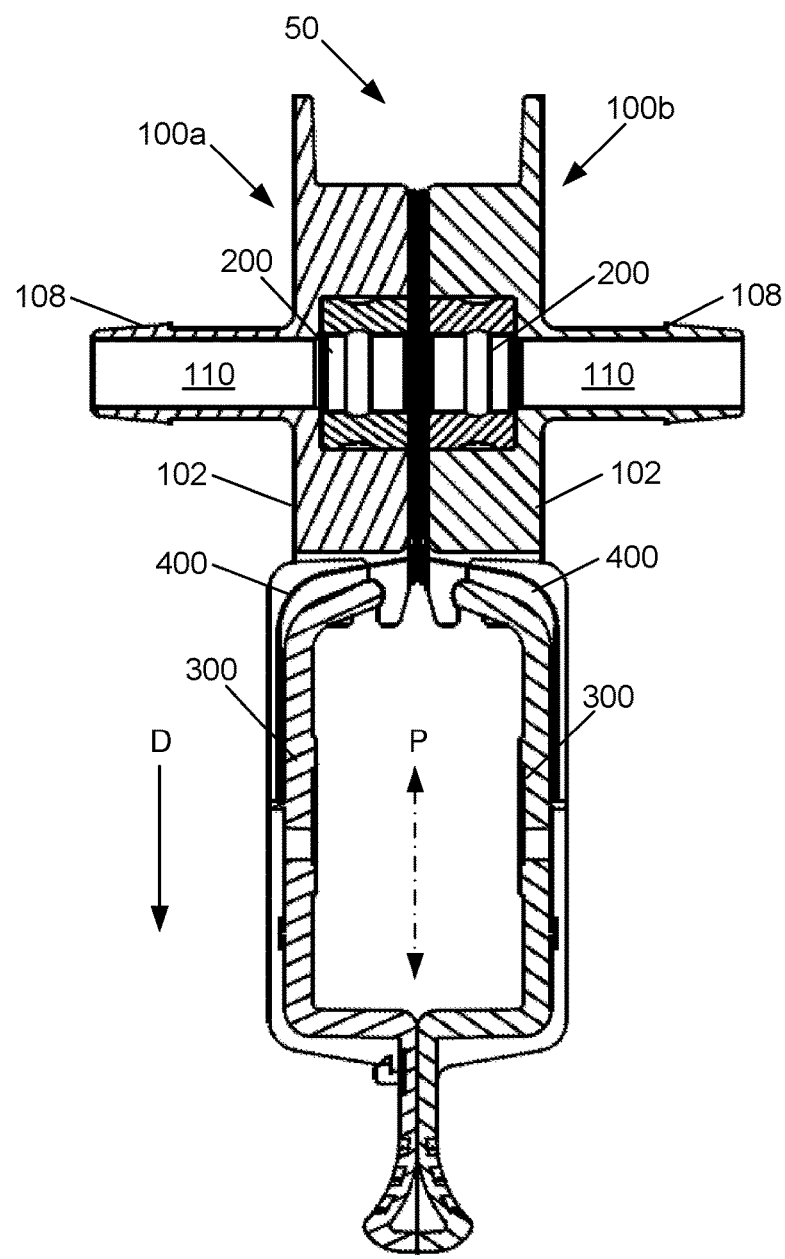
FIG. 4 is a cross-sectional side view of the aseptic coupling arrangement of FIG. 2.
Figure 5:
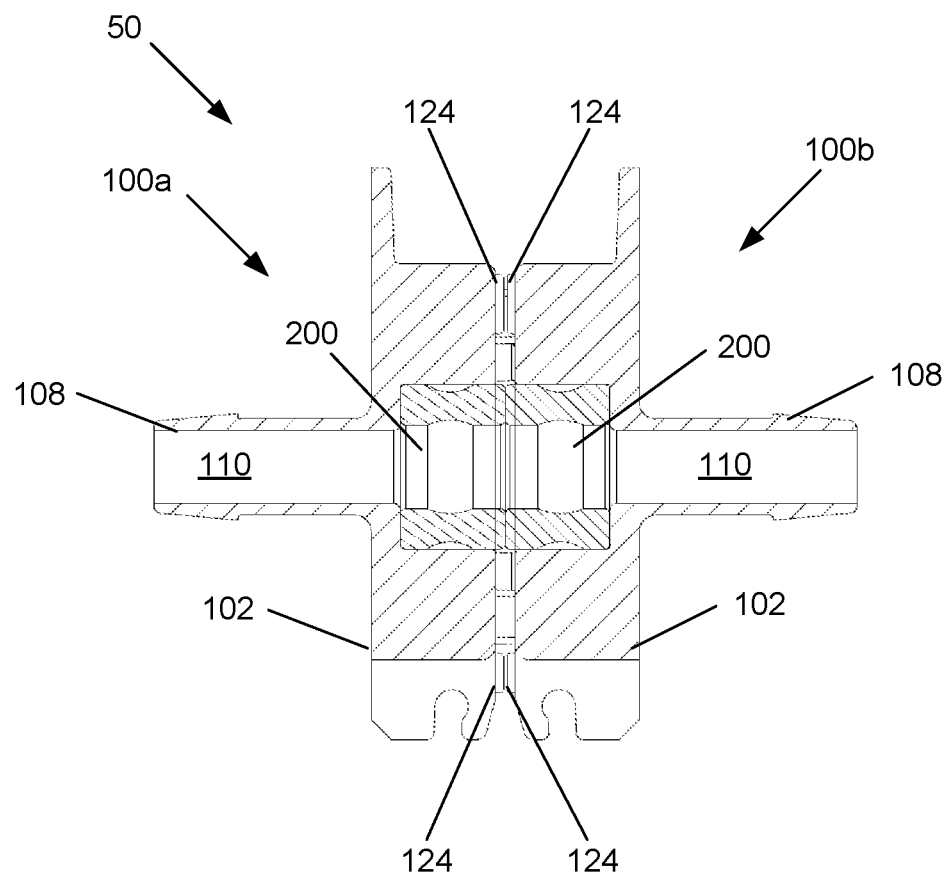
FIG. 5 is a cross-sectional view of the aseptic coupling arrangement of FIG. 2 in a coupled state.
Figure 6:
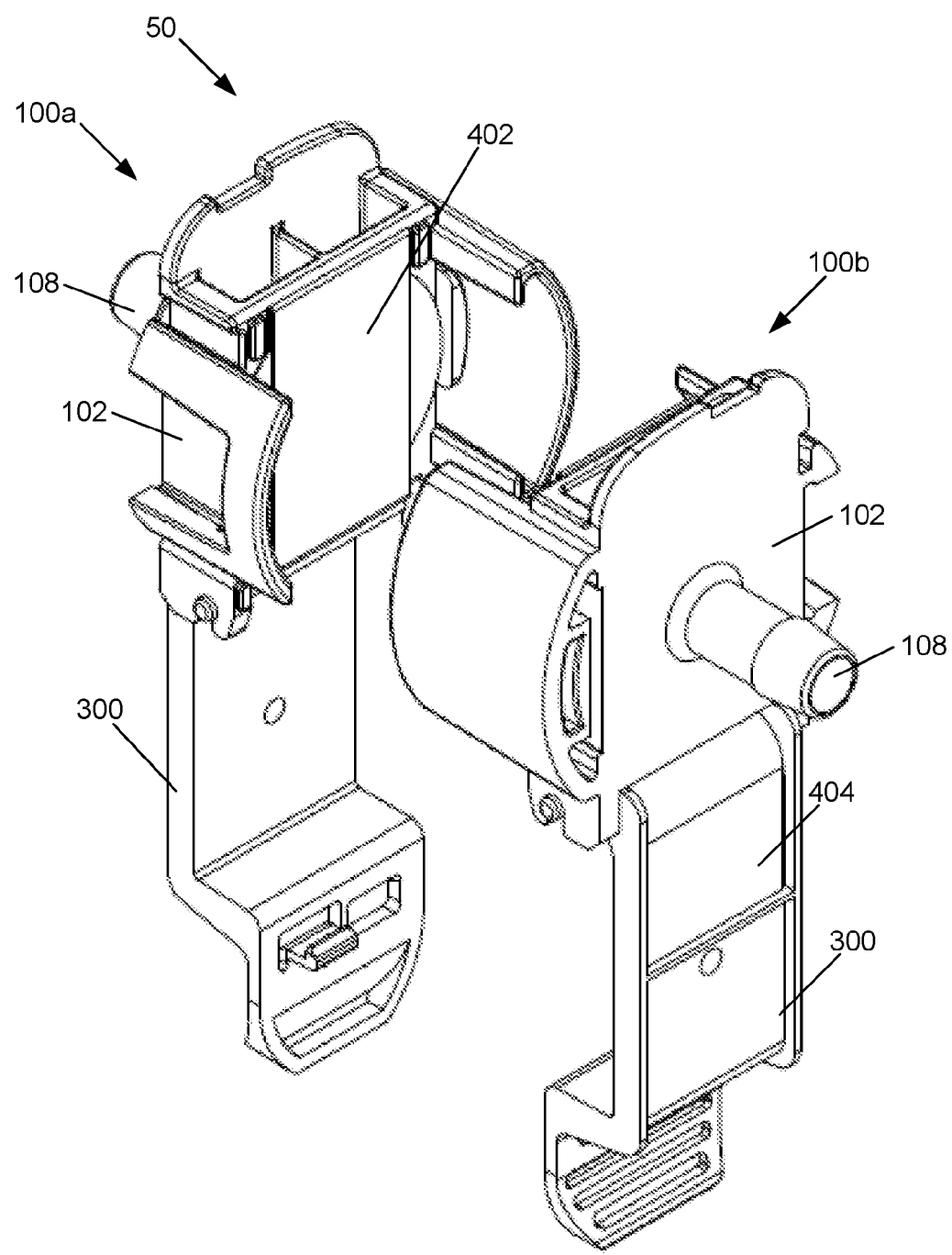
FIG. 6 is a perspective view of the aseptic coupling arrangement of FIG. 2 in an uncoupled state.
Figure 7:
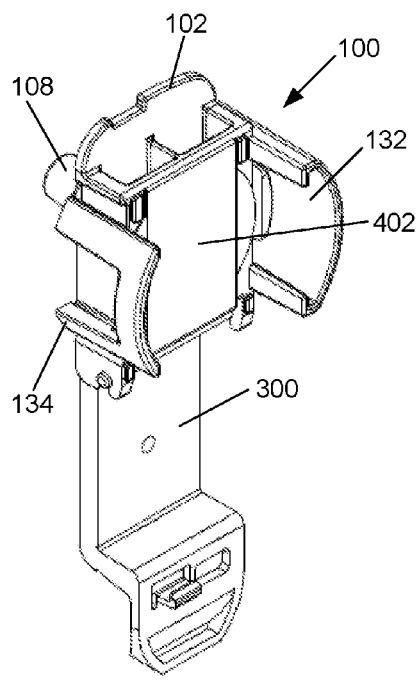
FIG. 7 is a front perspective view of a main body and protective cover of one coupling device of the aseptic coupling arrangement of FIG. 2, with the protective cover being in an open position.
Figure 8:
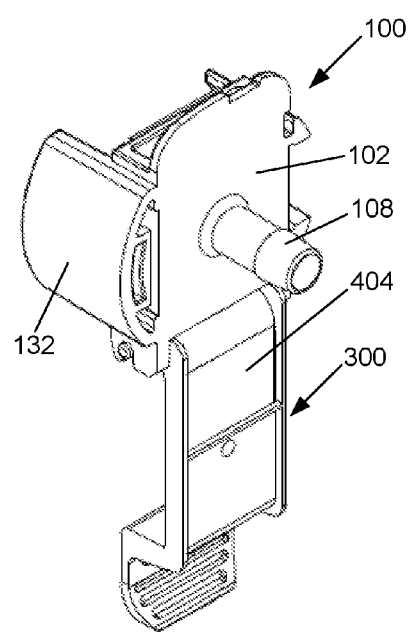
FIG. 8 is a rear perspective view of the main body and protective cover of the coupling device of FIG. 7, with the protective cover being in an open position.

The aseptic coupling arrangement 50 can be placed in an uncoupled state, a pre-coupled state and in a coupled state. FIG. 6 shows the aseptic coupling arrangement 50 in an uncoupled state wherein the coupling devices 100a, 100b are aligned but not yet connected to each other in any way. In the pre-coupled state, as shown in FIGS. 2-4, the devices 100a, 100b are connected to each other, but a fluid pathway through them is blocked by a membrane 400 sealed onto each of the coupling devices 100a, 100b. In the coupled state, as shown in FIG. 5, the membranes 400 are removed and a sterile fluid pathway is established between equipment 20 and equipment 30. Once the sterile fluid pathway is established, fluid can be transferred from equipment 20 to equipment 30, or vice versa.

In the example embodiments shown, the aseptic coupling devices 100a and 100b are of similar construction. As such, coupling devices 100a and 100b may be individually referred to as coupling device 100 herein for ease of reference. However, it is noted that each aseptic coupling device 100a, 100b may be provided with different features than the other, as desired.

Figure 9:
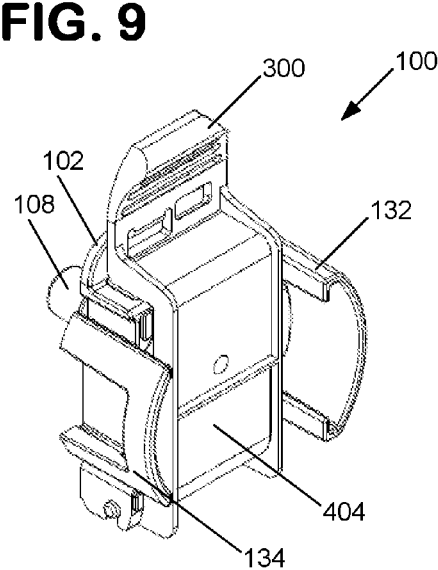
FIG. 9 is a front perspective view of the main body and protective cover of the coupling device of FIG. 7, with the protective cover being in a closed position.
Figure 10:
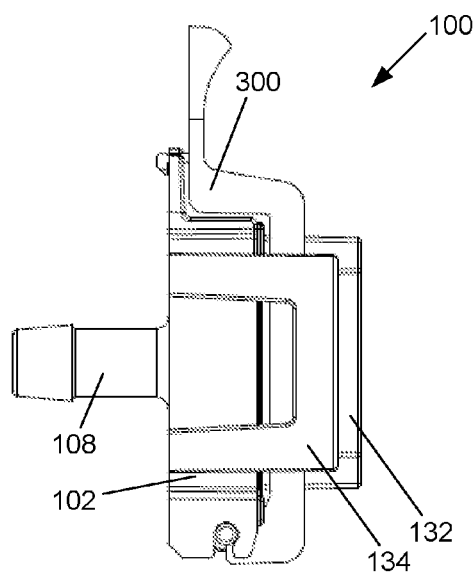
FIG. 10 is a first side view of the main body and protective cover of the coupling device of FIG. 7, with the protective cover being in a closed position.
Figure 11:
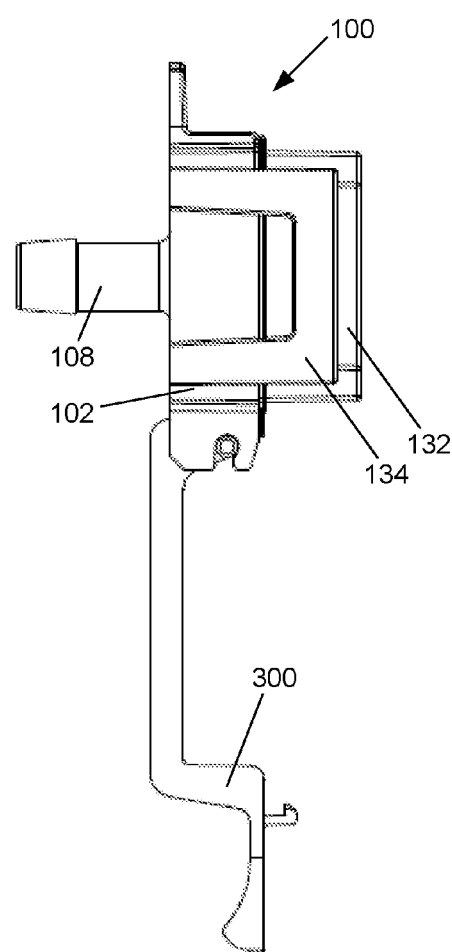
FIG. 11 is a first side view of the main body and protective cover of the coupling device of FIG. 7, with the protective cover being in an open position.
Figure 12:
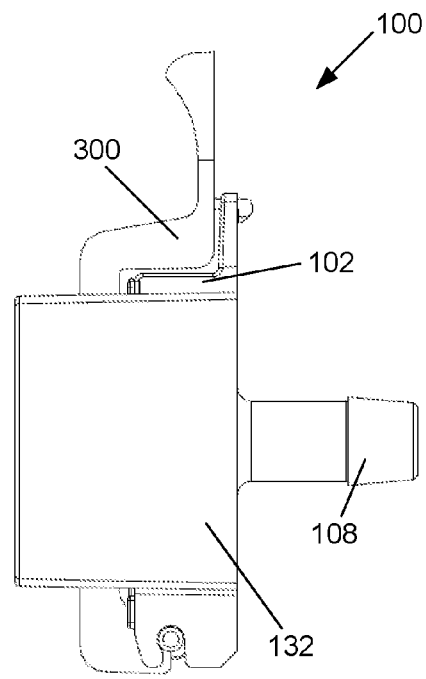
FIG. 12 is a second side view of the main body and protective cover of the coupling device of FIG. 7, with the protective cover being in a closed position.
Figure 13:
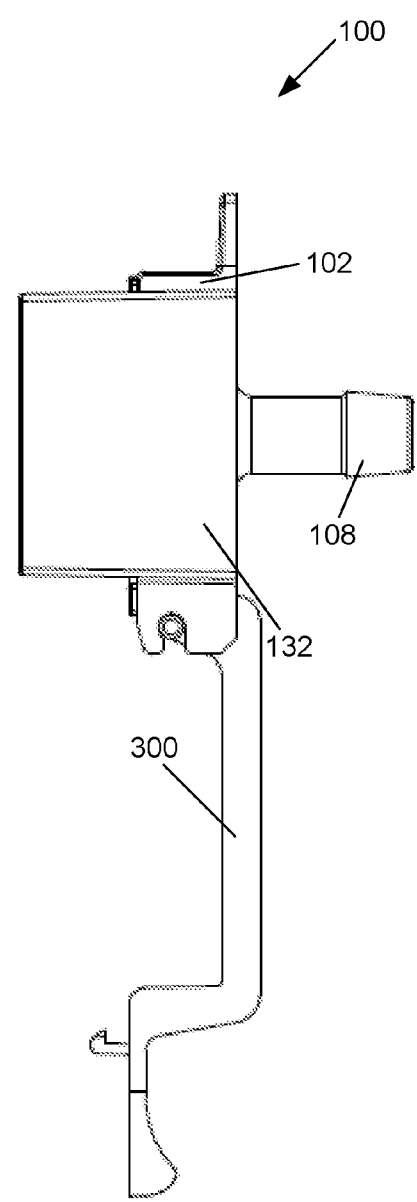
FIG. 13 is a second side view of the main body and protective cover of the coupling device of FIG. 7, with the protective cover being in an open position.
Figure 14:
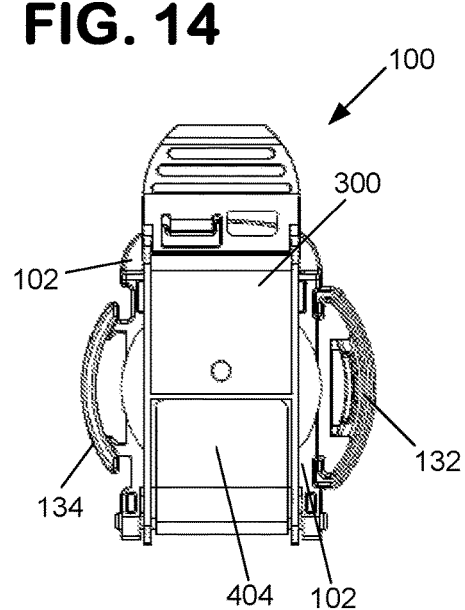
FIG. 14 is a front view of the main body and protective cover of the coupling device of FIG. 7, with the protective cover being in a closed position.
Figure 15:
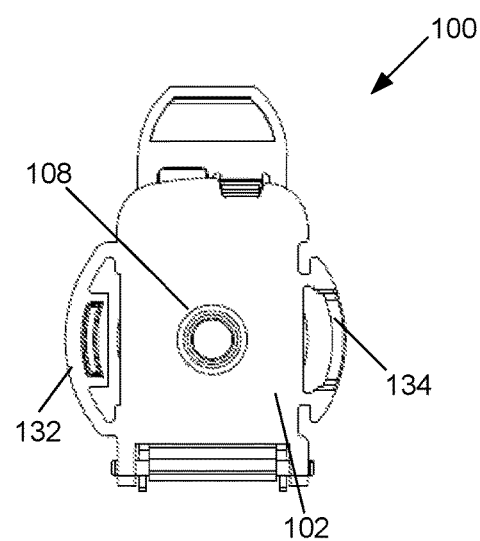
FIG. 15 is a rear view of the main body and protective cover of the coupling device of FIG. 7, with the protective cover being in a closed position.
Figure 16:
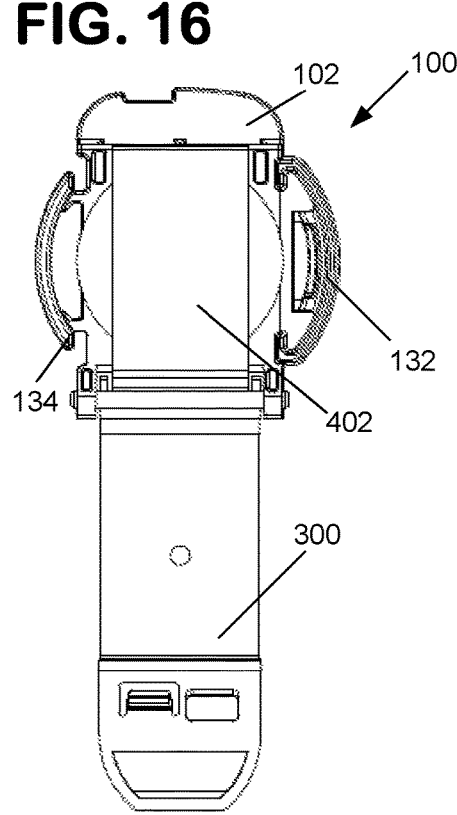
FIG. 16 is a front view of the main body and protective cover of the coupling device of FIG. 7, with the protective cover being in an open position.
Figure 17:
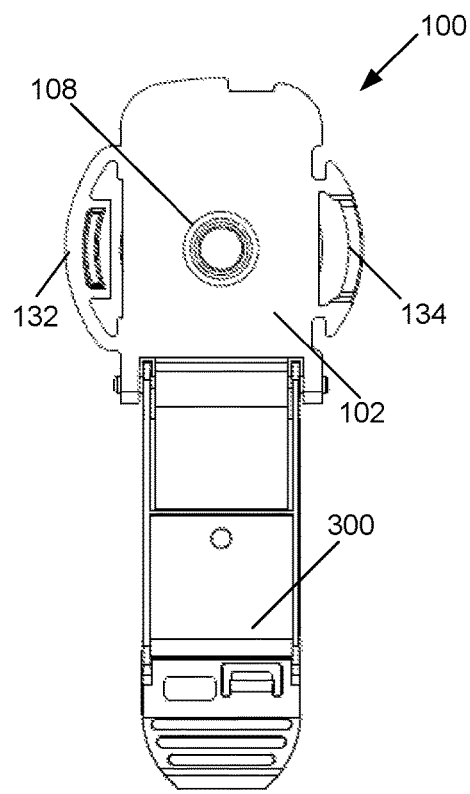
FIG. 17 is a rear view of the main body and protective cover of the coupling device of FIG. 7, with the protective cover being in an open position.
Figure 20:
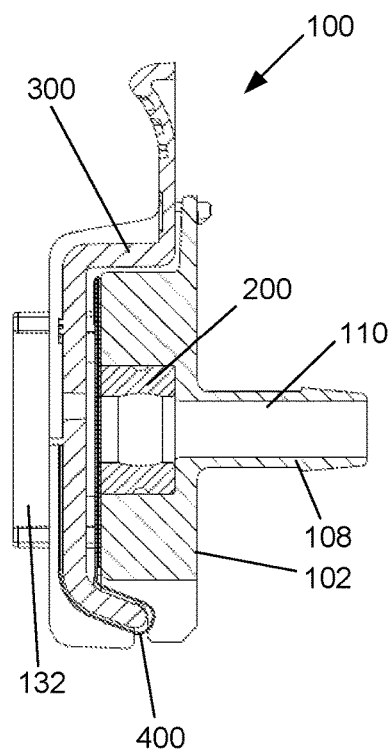
FIG. 20 is a second side cross-sectional view of the main body and protective cover of the coupling device of FIG. 7, with the protective cover being in a closed position.

As shown in a fully assembled state in FIGS. 7-23, coupling device 100 includes a main body 102, a sealing member 200 disposed within the main body 102. Coupling device 100 also includes a protective cover 300 removably connected to the main body 102. The cover 300 is rotatable with respect to the main body 102 between a closed position (see e.g. FIG. 9) and an open position (see e.g. FIG. 2). A membrane 400 is also provided on coupling device 100 that is removably connected to the main body 102 at a first end 402 and also connected to the protective cover 300 at a second end 404. Each of these features of coupling device 100 is described in further detail below.

Figure 24:
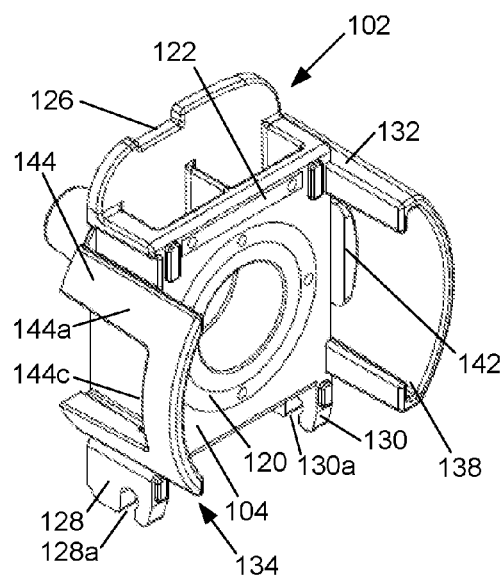
FIG. 24 is a front perspective view of the main body shown in FIG. 7.
Figure 25:
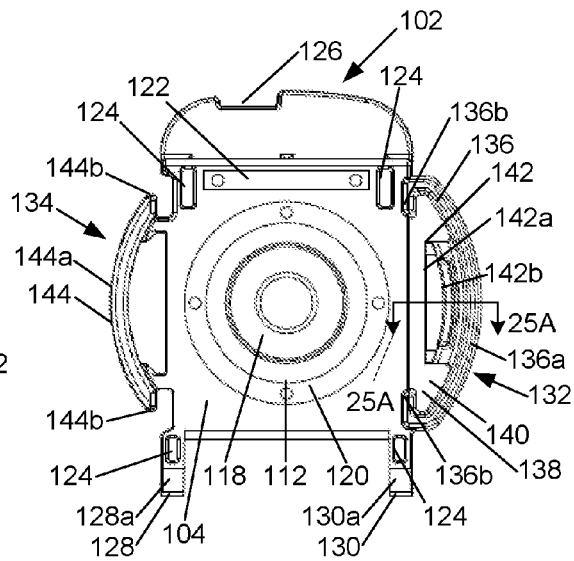
FIG. 25 is a front view of the main body shown in FIG. 7.
Figure 26:
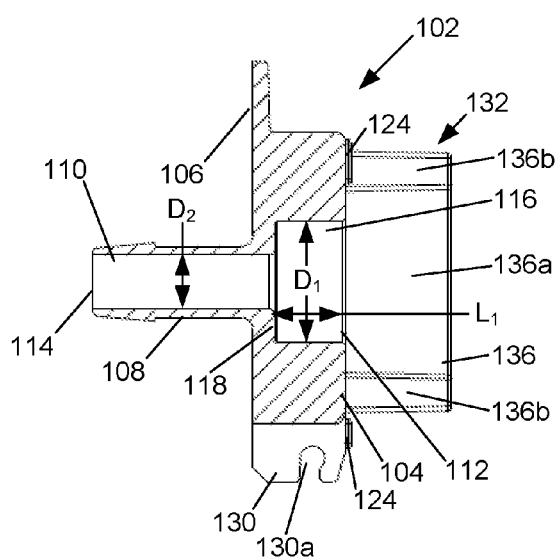
FIG. 26 is a cross-sectional side view of the main body shown in FIG. 7.

As most easily viewed at FIGS. 24-26, the main body 102 has a front face 104 and a rear face 106 onto which a conduit connection 108 is formed. A fluid passageway 110 within the main body 102 is defined between a first open end 112 and a second open end 114. As most easily seen at FIG. 26, the main body 102 defines a recess 116, having a first internal diameter $D_1$, for receiving a sealing member 200, discussed later. Conduit connection 108 defines a second internal diameter $D_2$ along fluid passageway 110. The second diameter $D_2$ is provided at a dimension that is generally about the same as the nominal internal diameter of the conduit to which the main body 102 is designed for connection. For example, $D_2$ can be designed to provide a ¼ inch diameter flow. At a location where the first and second internal diameters $D_1$, $D_2$ adjoin, a seal seat 118 is formed at a depth $L_1$ from the front face 104 for supporting and forming a seal with sealing member 200.

Figure 35:
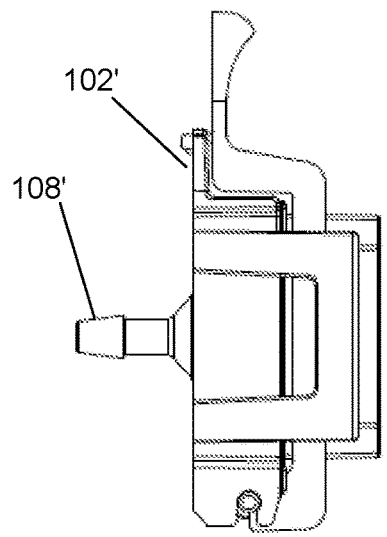
FIG. 35 is a side view of a second embodiment of a main body suitable for use in the coupling device shown in FIG. 7.
Figure 36:
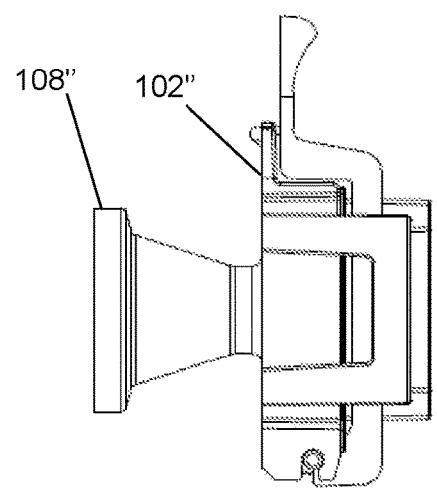
FIG. 36 is a side view of a third embodiment of a main body suitable for use in the coupling device shown in FIG. 7.
Figure 37:
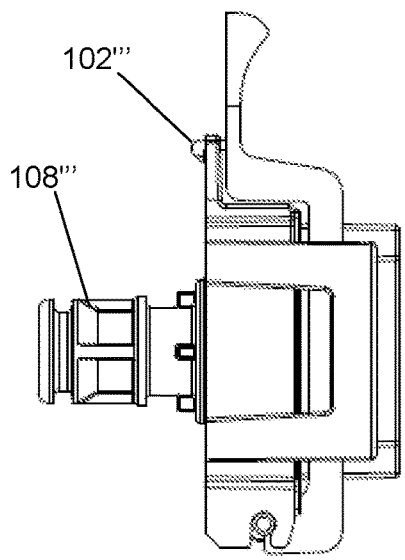
FIG. 37 is a side view of a fourth embodiment of a main body suitable for use in the coupling device shown in FIG. 7.

As stated previously, the second end 114 of the fluid passageway 110 is configured to be connected to a fluid pathway via the conduit connection 108. In the example shown, the conduit connection is barbed to form an HB type connection so that the main body 102 can be connected to a fluid pathway (e.g., 22) such as a tube or hose of a specified diameter, for example ⅛ inch, ¼ inch, and ⅜ inch. Other larger sizes are also possible, such as ½ inch, ⅝ inch, ¾ inch, 1 inch, etc. In the embodiment shown at FIGS. 2-26, conduit connection 108 is sized for a ¼ inch connection. FIG. 35 shows a conduit connection 108' provided on a main body 102' that is sized for a ⅛ inch connection. Instead of a barbed connection feature, many other types of connections known in the art may be provided, for example, sanitary, flared, threaded, quick connect, and compression type connections. To further illustrate such options, FIG. 36 shows a sanitary conduit connection 108" provided on a main body 102" while FIG. 37 shows a quick-connect type conduit connection 108''' provided on a main body 102'''. Conduit connection 108 may also be provided as a female type connection. In yet other examples, the connection can be a quick-connect type body with a latch and valving. This allows the body to be coupled to a male insert mounted to the conduit during fluid flow. Upon completion, removal of the male from the quick-connect type body causes the valve to close, thereby creating a valved disconnect.

Still referring to FIG. 24-26, the front face 104 of the main body 102 further includes a plurality of stand-off protrusions 124 configured to engage a corresponding plurality of stand-off protrusions 124 on the front face 104 of another main body 102 under certain conditions. For example, at least some of the opposing stand-off protrusions 124 will come into contact with each other when the main bodies 102 are over compressed together and/or when a side load is imparted on one or both of the main bodies 102. In the pre-coupled and coupled positions, opposing protrusions 124 are not ordinarily in contact with each other when no external forces are present, thus allowing the seals 200 to be fully engaged and compressed against each other due to the connectors 132, 134 (discussed later) on the main bodies 102. As such, stand-off protrusions 124 help to stabilize the connection to reduce the possibility of side load induced leakage. One skilled in the art, upon learning of the disclosed concepts presented herein, will appreciate that more or fewer stand-off protrusions may be provided on each face to ensure the same stated functionality.

Figure 4A:
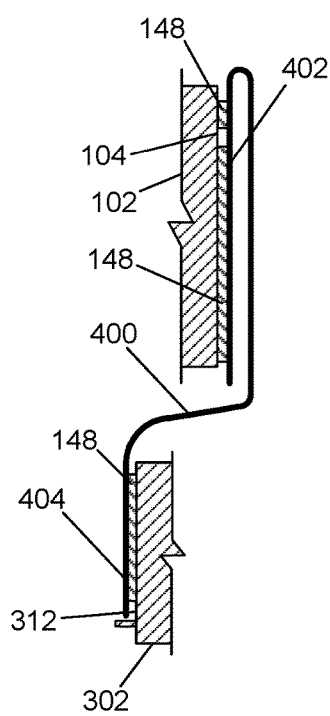
FIG. 4A is a schematic side view of a membrane suitable for use with the aseptic coupling arrangement of FIG. 2.
Figure 4B:
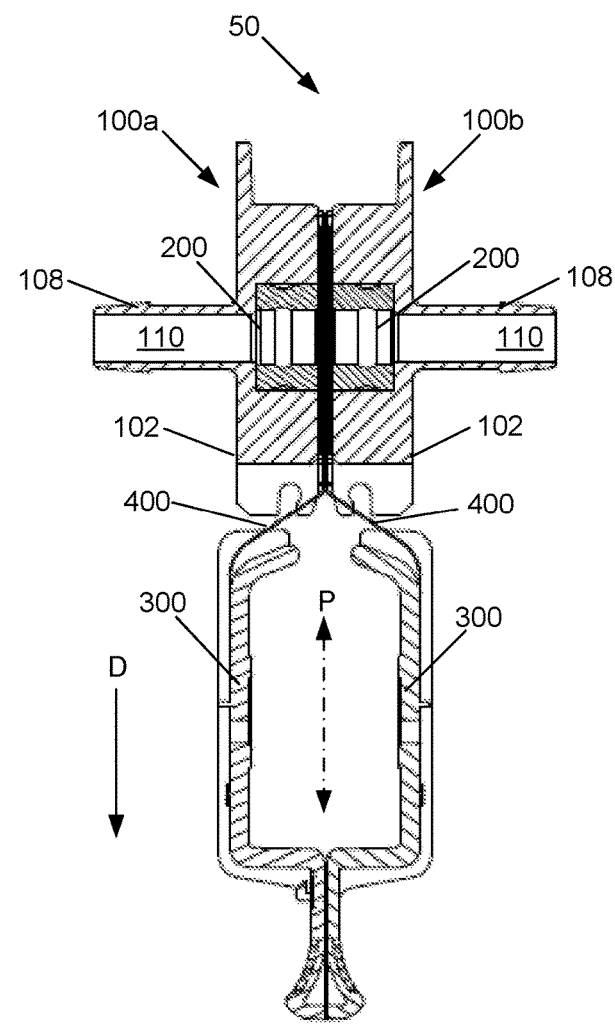
FIG. 4B is a cross-sectional side view of the aseptic coupling arrangement of FIG. 2, with cover portions removed from the main bodies of the coupling arrangement.

The front face 104 of the main body 102 may be provided with surface locations 120, 122 to allow for the first end 402 of the membrane 400 to be attached to the front face 104. In examples, the membrane 400 is coupled to the front face 104 completely around and beyond the first open end 112 of the main body 102 at attachment locations 120, 122. The attachment locations 120,122 allow membrane 104 to extend beyond the opening in the open end 112 so that as membrane 400 is removed, the sterility of open end 112 is maintained. In one embodiment, the surface locations 120, 122 are provided with an adhesive 148 to which the membrane 400 is adhered in a folded over arrangement, as shown schematically in FIG. 4A. In one embodiment, the adhesive 148 can be provided on the membrane 400 which can be subsequently attached to surface locations 120, 122. In one embodiment, the membrane 400 is heat welded to the front face 104. In such an embodiment, surface locations 120, 122 are not necessarily required.

As shown, the main body 102 is also provided with a notch 126 for engaging with a corresponding latch 306 on the protective cover 300 when the protective cover 300 is rotated into the closed position. Other arrangements for retaining the protective cover 300 in the closed position are possible. For example, a latch could be provided on the main body 102 and a notch could be provided on the protective cover 300.

Main body 102 is also provided with a pair of hinge members 128, 130 for retaining a corresponding hinge member 304 on the protective cover 300. As shown, hinge members 128, 130 each have an opening 128a, 130a into which the hinge member 304 can be pressed for a snap fit. Once snapped into position, the protective cover 300 can rotate with respect to the main body 102 between the open and closed positions. When the protective cover 300 has been rotated into the open position, the protective cover 300 may be pulled downward (i.e. in a direction D parallel to the front face 104 of the main body 102 as shown at FIGS. 3-4) and snapped out of the hinge members 128, 130 to separate the protective cover 300 from the main body 102. It is noted that, instead of the shown configuration, that hinge members 128, 130 may have a male type configuration while the hinge member 304 may have a female configuration. Additionally, fewer or more hinge members 128, 130, and 304 may be provided.

In order to enable the main body 102 of a first coupling device 100a to be connected to the main body 102 of a second coupling device 100b, a first connector 132 and a second connector 134 may be provided. In the embodiment shown, first and second connectors 132, 134 are located on opposite sides of the front face 104 of the main body 102. The connectors 132, 134 are designed to be engaged with each other and to ensure proper alignment of the front faces 104 of the coupling devices 100a, 100b. Accordingly, when the first coupling device 100a is oriented with its front face 104 facing the front face 104 of the second coupling device 100b, the second connector 134 of the first coupling device 100a will engage with the first connector 132 of the second coupling device 100b. Likewise, the second connector 134 of the second coupling device 100b will engage with the first connector 132 of the first coupling device. Many types of connectors that perform the functions of engagement and alignment may be utilized without departing from the concepts presented herein.

Figure 25A:
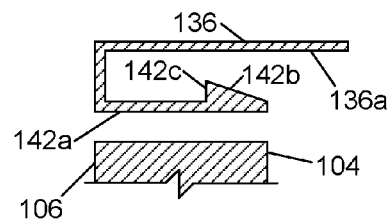
FIG. 25A is a cross-sectional view of a portion of the main body of FIG. 7, taken along section line 25A-25A shown in FIG. 25.
Figure 27:
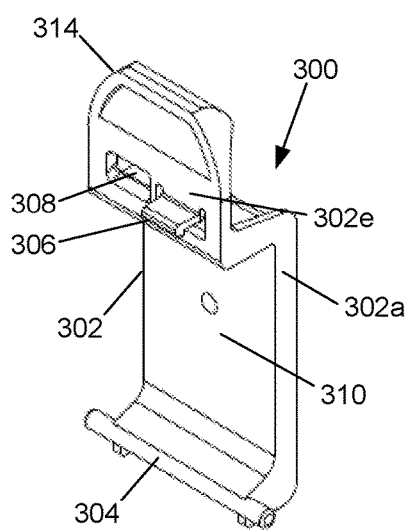
FIG. 27 is a front perspective view of the protective cover shown in FIG. 7.
Figure 28:
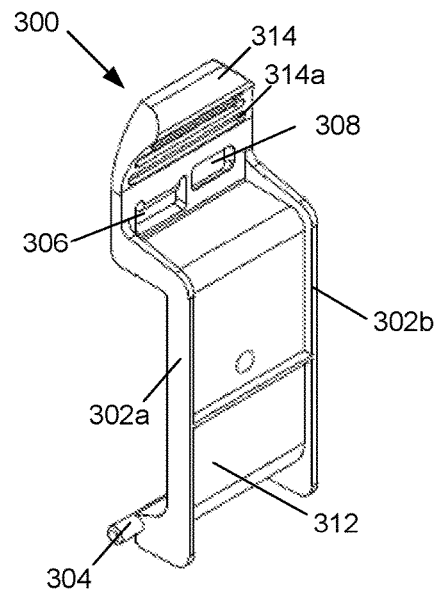
FIG. 28 is a rear perspective view of the protective cover shown in FIG. 7.
Figure 29:
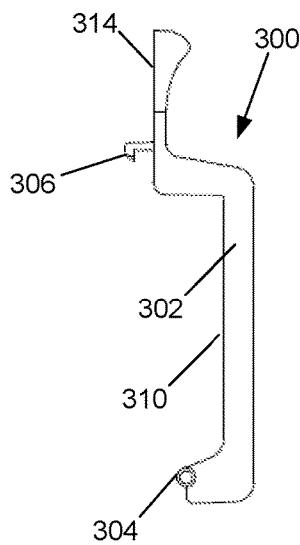
FIG. 29 is a side view of the protective cover shown in FIG. 7.
Figure 30:
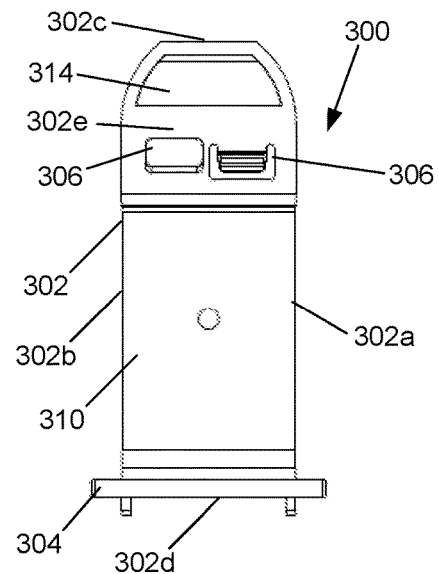
FIG. 30 is a front view of the protective cover shown in FIG. 7.
Figure 31:
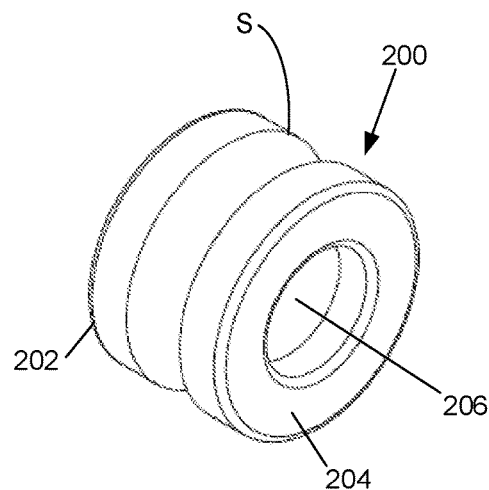
FIG. 31 is a perspective view of a sealing member receivable in the main body shown in FIG. 7.
Figure 32:
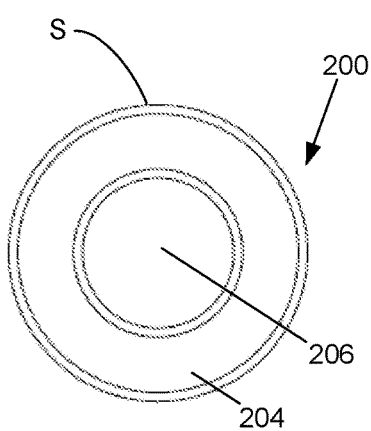
FIG. 32 is a front view of the sealing member shown in FIG. 31.
Figure 33:
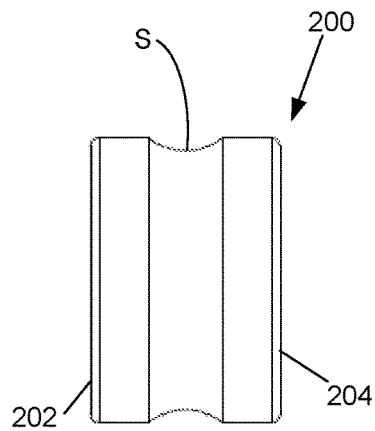
FIG. 33 is a side view of the sealing member shown in FIG. 31.
Figure 34:
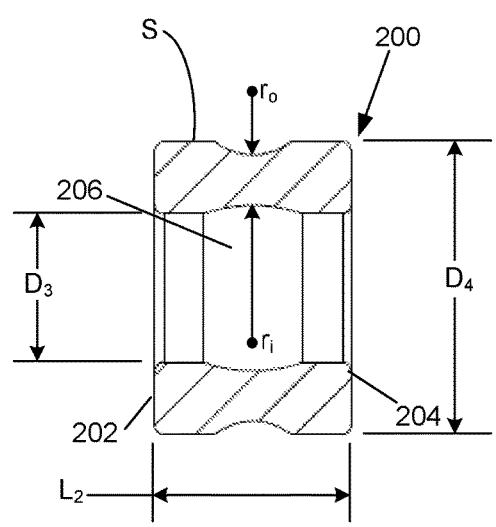
FIG. 34 is a cross-sectional side view of the sealing member shown in FIG. 31.

In the exemplary embodiment shown, the first connector 132 includes an extension 136 with a curved main portion 136a and side portions 136b that together form a channel 138. The channel 138 defines an interior volume 140 within which a latch member 142 is provided. As can be best seen at FIG. 25A, the latch member 142 has an extension 142a, a ramped surface 142b, and a locking surface 142c. The ramped surface 142b, as oriented in the embodiment shown, faces towards the curved main portion 136a of the extension 136.

The second connector 134 includes an extension 144 located on the opposite side of the front face 104 from which the first connector extends. The extension 144 has a curved main portion 144a and side edges 144b. The curved main portion 144a of the second connector 134 is configured to be received within the interior volume 140 of the channel 138 of the first connector 132. Proper alignment between two mating main bodies 102 is ensured by the side portions 136b of the first connector extension 136 which surround and guide the side edges 144b of the second connector extension 144.

The extension 144 of the second connector 134 also has a latch engaging surface 144c for engaging with the locking surface 142c of the latch member 142 such that two mated main bodies 102 cannot be separated once placed in the pre-coupled state. Accordingly, as the front faces 104 of each coupling device 100a, 100b are pressed towards each other, the latch members 142 engage the latch engaging surfaces 146 to secure the devices 100a, 100b together in a pre-coupled state. This action also provides an audible clicking sound to provide an indication to a user that the pre-coupled state has been achieved. In this state, the sealing members 200 of each device 100a, 100b are compressed against each other with membranes 400 therebetween.

Other arrangements of the latching member and the latch engaging surface are possible. For example, the latch engaging surface 144c could be provided on the first connector 132 with the latch member 142 being provided on the second connector 134. Alternatively, the first coupling device could be provided with first and second connectors that are substantially similar to each other wherein the second coupling device is also provided with substantially similar first and second connectors configured to engage with those on the first coupling device. However, it should be understood that the disclosed embodiments allow for the production of a single main body for both coupling devices 100a, 100b. Such a configuration can allow for better economies of scale, less inventory management, improved system flexibility, and less required training. Connectors other than latches may also be utilized.

With reference to FIGS. 31-34, sealing member 200 is shown in further detail. In the embodiment shown, the sealing member 200 has a length $L_2$ extending between a first face 202 and a second face 204 that is slightly greater than the length $L_1$ of the recess 116 of the main body 102. The greater length of the sealing member 200 ensures that the sealing member 200 makes sufficient contact with a corresponding sealing member 200 in a second main body 102 to form an aseptic seal. Sealing member 200 also has a central opening 206 having an internal diameter $D_3$ that is about the same dimension as the diameter $D_2$ of the conduit connection 108. Sealing member 200 also has an external diameter $D_4$ that is about the same dimension as the diameter $D_1$ of the recess 116 in the main body 102. In one embodiment, external diameter $D_4$ is greater than length $L_2$. In one embodiment, external diameter $D_4$ is from about 1.25 times to about 1.75 times greater, for example about 1.5 times greater, than length $L_2$.

Sealing member 200 also has a sidewall S that has a reduced thickness at the midpoint of the sidewall S. On the exterior portion, the sidewall S has a reduced thickness defined by an outside radius $r_o$. On the interior portion, the sidewall S has a reduced thickness defined by an inside radius $r_i$. In one embodiment, the dimension of the inside radius $r_i$ is greater than the dimension of the outside radius $r_o$. In one embodiment, the dimension of the inside radius $r_i$ is equal to or greater than twice the dimension of the outside radius $r_o$, for example about 2.4 times larger. In one embodiment, the inside radius $r_i$ is between about 0.2 inch to about 0.3 inch, for example about 0.26 inch. In one embodiment, the outside radius $r_o$ is between about 0.1 inch to about 0.25 inch, for example about 0.11 inch.

Where the inside radius $r_i$ is greater than the outside radius $r_o$, the seal structure enhances the axial compression performance of the sealing member 200 (compressed between the seal seat 118 at first face 202 and another sealing member 200 at second face 204) while ensuring that flow through the sealing member 200 is not restricted by the unintended formation of an inwardly extending bulge under compression. Because the inside radius $r_i$ is larger than the exterior radius $r_o$, a compressive force on the seal against faces 202, 204 will tend to cause the sidewall S to deflect outwardly away from the central opening 206 of the seal 200. Accordingly, the internal flow path through the seal 200 is not unnecessarily constricted by compression of the seals 200. Such a structure is especially useful where a mechanical sensor may be inserted through the central opening 206 of the seal. The described seal structure also provides for enhanced sealing when the system is pressurized.

With reference to FIGS. 27-30, the protective cover 300 is shown in further detail. The protective cover 300 serves two primary functions. The first function is to protect the membrane 400, the sealing member 200, and the front face 104 of the main body 102 when the coupling device 100 is in an uncoupled or isolated state. To serve this purpose, the protective cover 300 is placed in the closed position so that at least a portion of the membrane 400 is covered by the cover 300. The second function is to provide a means for removing membranes 400 after the first and second coupling devices 100a, 100b have been placed in the pre-coupled state. To serve this purpose, the protective cover 300 is placed in the open position. In the open position, the portion of the membrane 400 covering the main body front face 104 is exposed.

Figure 21:
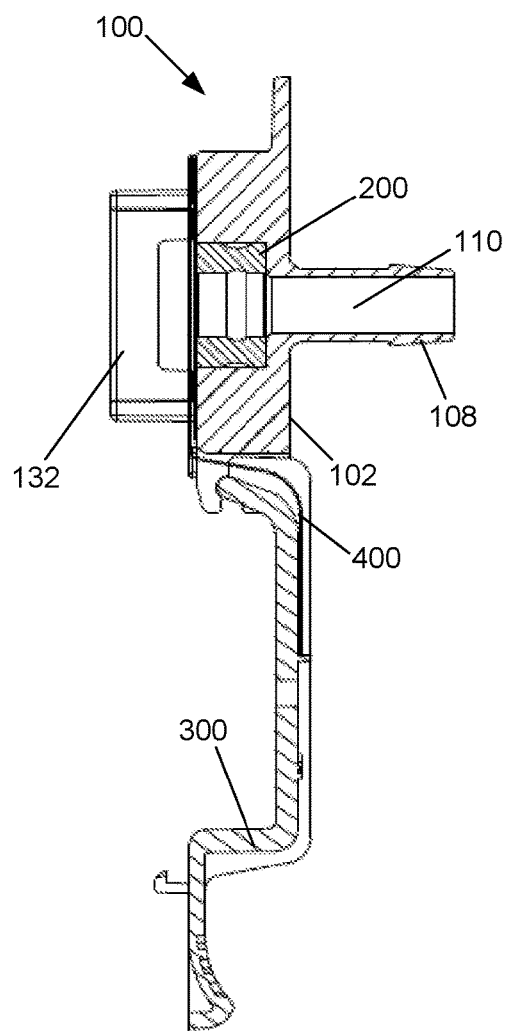
FIG. 21 is a second side cross-sectional view of the main body and protective cover of the coupling device of FIG. 7, with the protective cover being in an open position.
Figure 22:
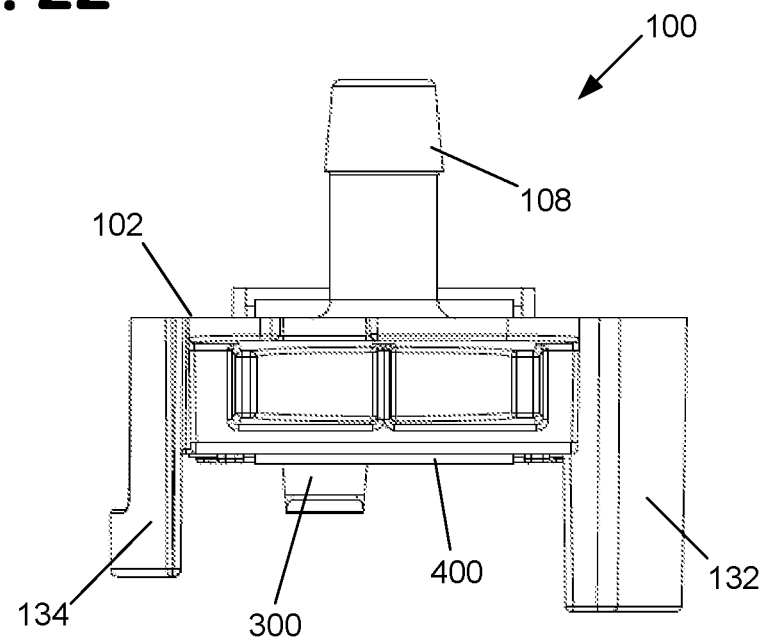
FIG. 22 is a top view of the main body and protective cover of the coupling device of FIG. 7, with the protective cover being in an open position.
Figure 23:
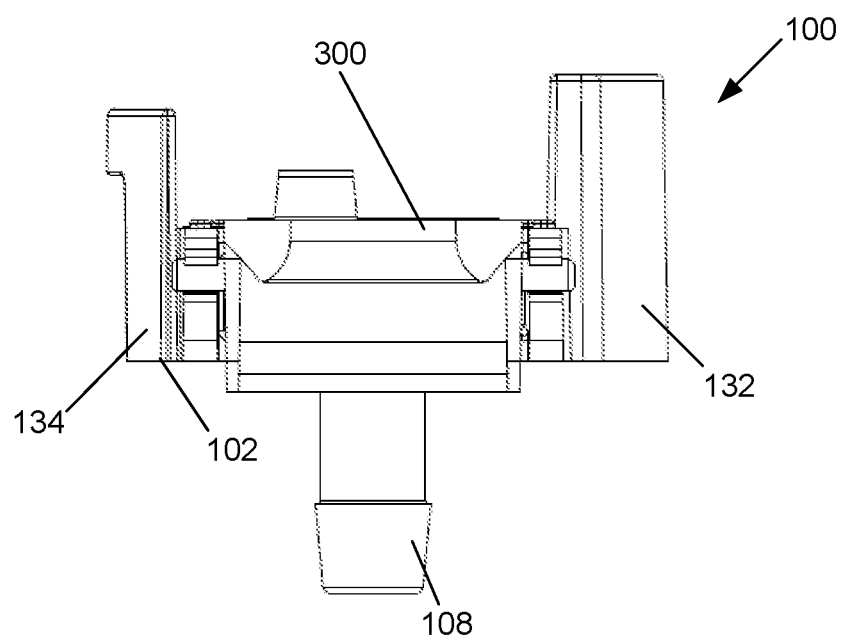
FIG. 23 is a bottom view of the main body and protective cover of the coupling device of FIG. 7, with the protective cover being in an open position.

In the embodiment shown, the protective cover 300 has a main body 302 extending between a first side 302a, a second side 302b and between a first end 302c and a second end 302d. The main body 302 also defines a first surface 310 and a second surface 312. The first surface 310 faces the front face 104 of the main body 102 of the coupling device 100 when the protective cover 300 is in the closed position. Accordingly, the first surface 310 operates to protect the membrane 400, the sealing member 200, and the front face 104 of the main body 102. Additionally, when the cover 300 is in the closed position, the first surface 310 slightly compresses sealing member 200 which relieves pressure that sealing member 200 would otherwise exert on membrane 400. This compressed state of sealing member 200 is most easily seen at FIGS. 18 and 20. FIGS. 19 and 21 show the sealing member 200 in a more relaxed state even though membrane 400 still covers the sealing member 200.

The second surface 312 of the protective cover 300 is provided to allow for the second end 204 of the membrane 400 to be attached to the protective cover 300. In one embodiment, second surface 312 is provided with an adhesive 148 to which the membrane is adhered. In one embodiment, the adhesive 148 can be provided on the membrane 400 which can be subsequently attached to second surface 312. See FIG. 4A for an example arrangement of membrane 400 with respect to the second surface 312. In one embodiment, the membrane 400 is heat welded to the second surface 312. The connection of the membrane 400 to the protective cover 300 is sufficiently secure to retain the membrane 400 onto the protective cover 300 when removing the membrane 400 from the front face 104 of the coupling device main body 102. This result is largely accomplished by the rolled over arrangement of the membrane 400 with respect to the main body 102. This arrangement allows for membrane 400 to be peeled off the front face 104 in a direction D with significantly less force than would be required to shear the second end 404 of the membrane 400 from the protective cover second surface. It is also noted that a strength difference may be acquired by using specific adhesives and/or by manipulating the relative surface areas of the portions of the membrane that are actually attached to the cover 300 and main body 102.

As stated previously, the main body 302 at the second end 302d is provided with a hinge member 304 that can be received in the hinge members 128, 130 of the main body 102. At the first end 302c of the main body 302, a handle member 314 is provided. Handle member 314 is for operating the protective cover 300 between the open and closed positions, and for use as a gripping member when pulling the protective cover 300 away from the main body 102 of the coupling device 100. As shown, handle member 314 includes surface features 314a, such as channels or ribs, for enhancing the ability of a user to grip and exert force on the handle member 314.

Each protective cover 300 is also provided with a locking tab 306 and a corresponding recess 308. As stated previously, the locking tab 306 can be snapped into or engaged with notch 126 of the coupling device main body 102. Additionally, the locking tab 306 can be snapped into the recess 308 of another protective cover 300 when two coupling devices 100a, 100b are placed in the pre-coupled position and when each protective cover 300 is in the open position, as shown in FIGS. 2-4. The attachment of the protective covers 300 to each other is enabled because, when in the open position, the face 302e of the cover body 302 at the location of tab 306 and recess 308 is generally in the same plane P as the main body front face 104. Once in this attached position, the protective covers 300 may be pulled in a downward direction D that is parallel to the front faces 104 via handle portions 314 to remove membranes 400 from the main body front faces 104 of the coupling devices 100a, 100b. As the membranes 400 are removed, the second faces 204 of the sealing members 200 come into contact with each other and form an aseptic seal. In this condition, the coupling devices 100a, 100b are now in the coupled state.

Because the protective covers 300 are locked together, this arrangement ensures that the membranes 400 will roll onto themselves and detach from the front faces 104 in a simultaneous or a near simultaneous fashion. However, it is noted that the membranes 400 can be removed in sequential fashion as well if the protective covers 300 are not secured together, although sterility may be compromised.

Figure 38:
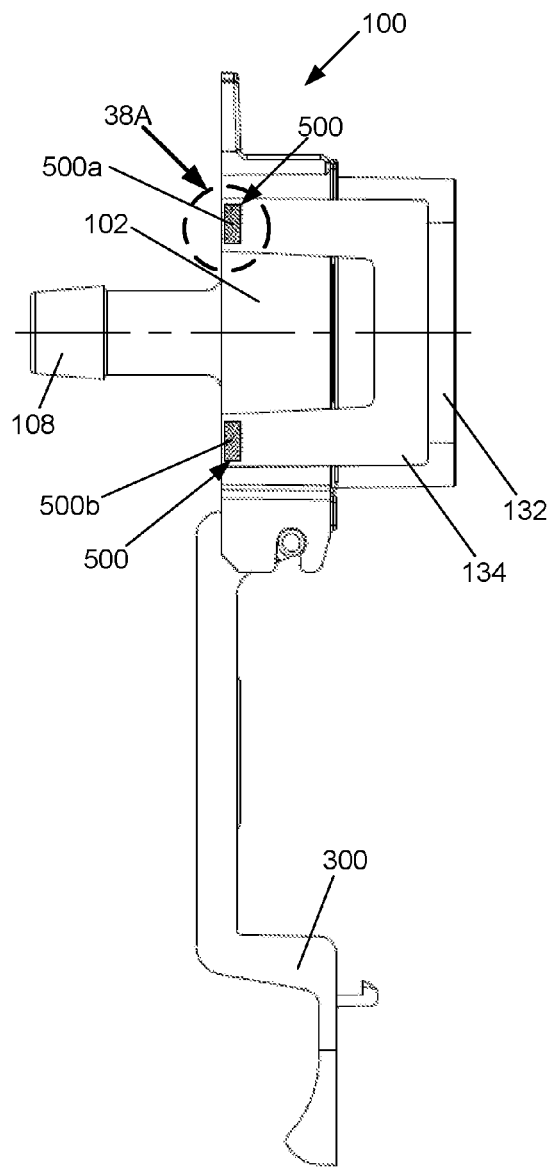
FIG. 38 is a first side view of the main body and protective cover of the coupling device of FIG. 7, with the protective cover being in an open position, wherein the main body further includes an optional visual indicator.
Figure 39:
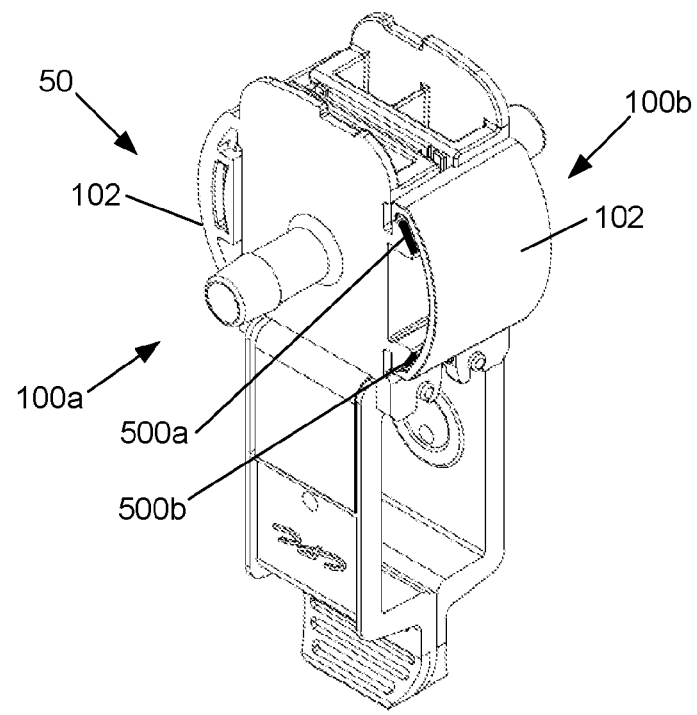
FIG. 39 is a perspective view of an aseptic coupling arrangement formed from two of the coupling devices of FIG. 7 having the optional visual indicator.
Figure 40:
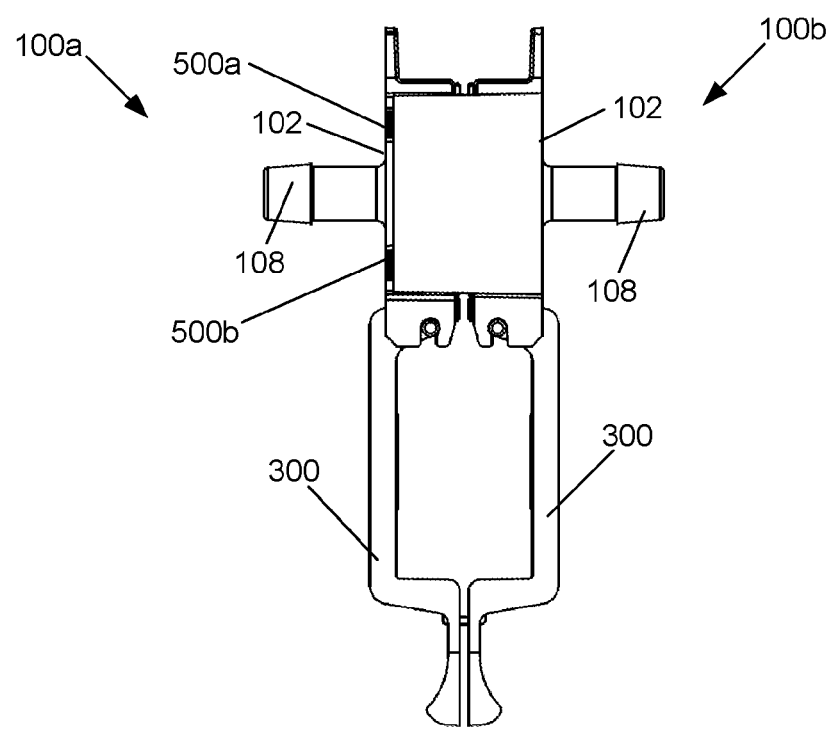
FIG. 40 is a side view of the coupling arrangement shown in FIG. 39.

Referring to FIGS. 38 to 40, an embodiment of a coupling device 100 including an optional visual indicator 500 is shown. The optional visual indicator 500 is for providing a visual indication that the coupling devices 100a, 100b have not been fully engaged into the pre-coupled position. Such a feature is beneficial in that an operator can verify that the coupling devices 100a, 100b are properly connected to each other prior to removing the membranes 400.

Figure 38A:
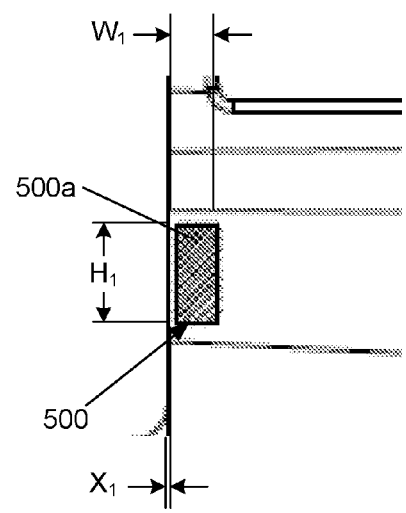
FIG. 38A is an enlarged side view of the coupling device and visual indicator shown in FIG. 38.

As best seen at FIGS. 38 and 38A, visual indicator 500 includes a first visual indicator 500a and a second visual indicator 500b, both of which are provided on the outer surface of the second connecting feature 134. As shown, each visual indicator 500 has a height $h_1$ and a width $w_1$. In one embodiment, height $h_1$ is from about 0.1 inch to about 0.2 inch, for example about 0.14 inch. In one embodiment, width $w_1$ is from about 0.01 inch to about 0.1 inch, for example about 0.06 inch.

As most easily seen at FIG. 38A, each visual indicator 500 can also be set back from the rear face 106 of the main body 102 by a distance $x_1$. If the visual indicator 500 is provided such that it extends all of the way to the rear face 106, a portion of the visual indicator 500 may be visible when viewed from an angle. As such, setting back the visual indicator 500 from the rear face 106 helps to ensure that no part of the visual indicator 500 is visible when the coupling devices 100a, 100b are placed in the pre-coupled position, even when viewed from an angle. In one embodiment, distance $x_1$ is from about 0.01 inch to about 0.1 inch, for example about 0.10 inch.

Because the second connecting feature 134 is entirely received within the first connecting feature 132 in the pre-coupled state, the visual indicators 500a, 500b are entirely obscured from view when the coupling devices 100a, 100b are successfully placed in the pre-coupled state. However, as can be seen at FIGS. 39-40, the indicators 500a, 500b are exposed when the coupling devices 100a, 100b are not fully engaged, even when not engaged by only a small distance. For example, the visual indicators 500a, 500b are easily visible even when the coupling devices 100a, 100b are separated by only 0.04 inch, as is the case in FIGS. 39-40.

Figure 41:
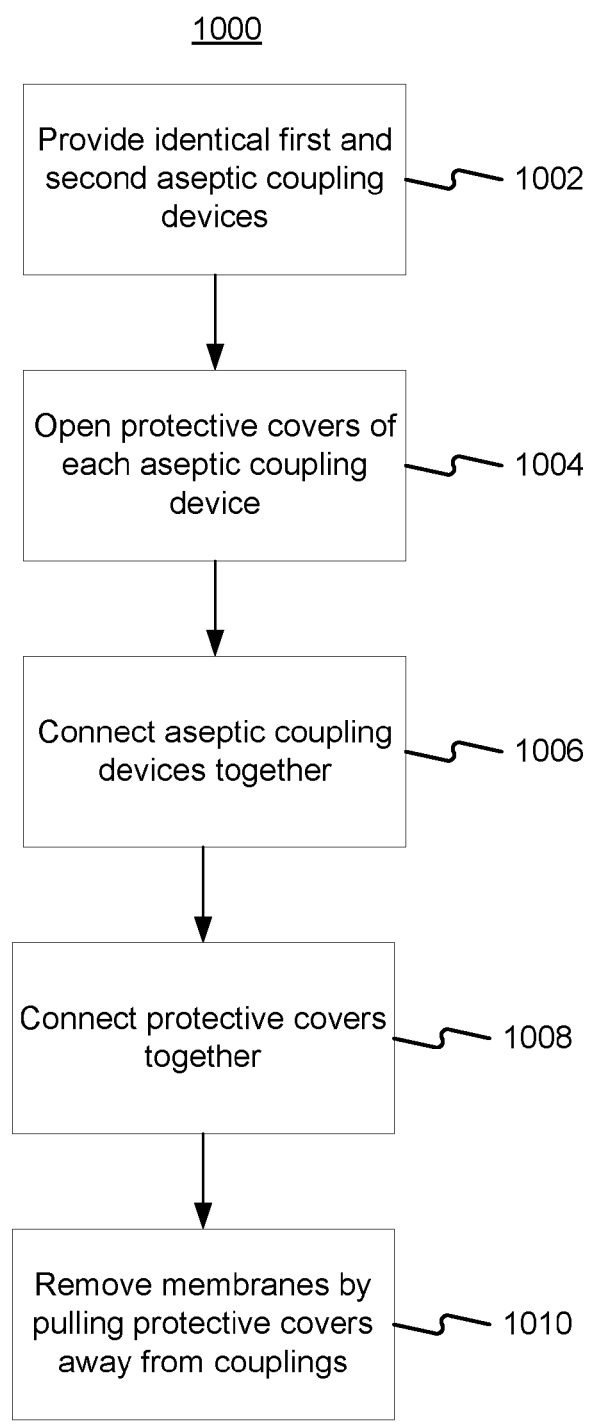
FIG. 41 is a flow diagram of a method of creating an aseptic coupling of a first coupling device and a second coupling device.

Referring now to FIG. 41, an example method 1000 for connecting aseptic coupling device 100a to aseptic coupling device 100b is shown.

First, at operation 1002, a first aseptic coupling device 100a and a substantially similar second aseptic coupling device 100a are provided. In one embodiment, each aseptic coupling device includes a main body 102 having an internal fluid passageway 110 and first and second connecting features 132, 134. A sealing member 200 at least partially received within the main body 102 is also included as is a removable membrane 400 attached to the main body 102 and covering the internal fluid passageway 110. Each aseptic coupling device also includes a removable cover 300 rotatably and removably attached to the main body 102 that is also attached to the removable membrane 400. In one embodiment, step 1002 includes providing first and second aseptic coupling devices 100a, 100b that are not identical to each other.

Second, at operation 1004, protective covers 300 of each aseptic coupling device are moved to an open position.

At operation 1006, the first and second aseptic coupling devices 100a, 100b are aligned with each other in an uncoupled state and then connected to each other to form a pre-coupled state, for example via connecting features 132, 134.

At operation 1008, the protective covers 300 are attached to each other while at operation 1010, the membranes 400 of each coupling device 100a, 100b are removed by detaching the protective covers 300 from the coupling devices 100a, 100b. As noted above, the removal of the membranes 400 allows for the sealing members 200 to engage with each other resulting in the formation of a sterile connection. It is also noted that steps 1008 may be eliminated and step 1010 may include removing the membranes one at a time in a sequential fashion although sterility may be compromised.

In example embodiments, the aseptic coupling devices and their respective covers are made of a polymeric material. For example, in one embodiment, the aseptic coupling devices are made of polycarbonate and the sealing members used therein are made of a silicone rubber. Other materials can be used.

In some embodiments, membrane 400 is autoclavable and gamma stable for sterilization. In various embodiments, membrane 400 is a composite design that consists of two components: 1 tag and 1 vent. The tag is a laminate including: a polyethylene terephthalate (PET) film, polyethylene (PE) foam, aluminum foil, and a sealing layer. The foam and/or foil may or may not exist in the final configuration. The sealing layer allows the tag to be bonded or welded to polycarbonate connectors (e.g., aseptic coupling devices 100a and 100b).

The vent is an expanded poly(tetrafluoroethylene) (ePTFE) membrane that will be bonded or welded onto the tag. Membrane 400 is located over the center of the flow area of aseptic coupling devices 100a and 100b, respectively, when the tags and vents are bonded or welded to connectors. The vent allows air and steam to flow into the system 10 during sterilization. The pore size of membrane 400 is such that membrane 400 filters out microorganisms larger than 0.2 microns.

In another embodiment, membrane 400 is a polyethersulfone (PES) and polyester laminate membrane. This membrane is hydrophobic and breathable. The pore size is such that microorganisms larger than 0.2 microns are filtered out. When bonded, the polycarbonate melts into the polyester fibers, so that the PES acts as the filter, and the polyester acts as the structure.

In other embodiments, membrane 400 is a Tyvek membrane that is coated on one side to allow membrane 400 to be bonded to polycarbonate connectors (e.g., aseptic coupling devices 100a and 100b). Tyvek is breathable in nature, so there is no need for an additional vent. Tyvek is a non-woven polyethylene membrane.

The various embodiments described above are provided by way of illustration only and should not be construed to limit the claims attached hereto. Those skilled in the art will readily recognize various modifications and changes that may be made without following the example embodiments and applications illustrated and described herein, and without departing from the true spirit and scope of the disclosure.

What is claimed is:

1. A coupling device, comprising:
   a main body defining a front face and a fluid passage therethrough;
   a membrane removably connected to and at least partially covering the front face; and
   a protective cover connected to the membrane, the protective cover removably connected to and abutting the main body, the protective cover being movable relative to the main body between: (i) a closed position in which the protective cover covers at least a portion of the membrane covering the front face, (ii) an open position in which the membrane covering the front face is exposed while the protective cover remains removably connected to the main body, and (iii) a position in which the protective cover is separated from the main body.

2. The coupling device of claim 1, further comprising a connecting feature disposed on the main body and configured to couple the coupling device to a second coupling device.

3. The coupling device of claim 1, further comprising a sealing member received at least partially within the main body.

4. The coupling device of claim 3, wherein, while the protective cover is in the closed position, the protective cover compresses the sealing member.

5. The coupling device of claim 1, wherein removal of the protective cover away from the main body causes the membrane to be removed from the front face.

6. The coupling device of claim 1, wherein the protective cover is rotatable about a hinge member between the closed position and the open position.

7. The coupling device of claim 1, wherein the protective cover includes a locking tab that releasably engages with the main body while the protective cover is in the closed position.

8. An aseptic coupling system, comprising:
   a. a first aseptic coupling device comprising:
      a first main body defining a first front face and a first fluid passage therethrough;
      a first membrane removably connected to and at least partially covering the first front face; and a first protective cover connected to the first membrane, the first protective cover removably connected to and abutting the first main body, the first protective cover being movable relative to the first main body between: (i) a closed position in which the first protective cover covers at least a portion of the first membrane covering the first front face, (ii) an open position in which the first membrane covering the first front face is exposed while the first protective cover remains removably connected to the first main body, and (iii) a position in which the first protective cover is separated from the first main body; and b. a second aseptic coupling device configured to couple with the first aseptic coupling device and comprising:
a second main body defining a second front face and a second fluid passage therethrough;
a second membrane removably connected to and at least partially covering the second front face; and
a second protective cover connected to the second membrane, the second protective cover removably connected to and abutting the second main body, the second protective cover being movable relative to the second main body between: (i) a closed position in which the second protective cover covers at least a portion of the second membrane covering the second front face, (ii) an open position in which the second membrane covering the second front face is exposed while the second protective cover remains removably connected to the second main body, and (iii) a position in which the second protective cover is separated from the second main body.

9. The aseptic coupling arrangement of claim 8, wherein the first and second protective covers are configured to be attached to each other such that the first membrane and the second membrane can be removed from the first front face and the second front face, respectively, at the same time.

10. The aseptic coupling arrangement of claim 9, wherein the first and second protective covers each include a locking tab and a corresponding recess that configures them to be attached to each other.

11. The aseptic coupling arrangement of claim 10, wherein the locking tab of the first protective cover is a first locking tab and the locking tab of the second protective cover is a second locking tab, wherein the first locking tab is engaged with a first notch of the first main body while the first protective cover is in the closed position, and wherein the second locking tab is engaged with a second notch of the second main body while the second protective cover is in the closed position.

12. The aseptic coupling arrangement of claim 8, wherein the first main body includes a first connecting feature, wherein the second main body includes a second connecting feature, wherein the first and second connecting features each include a first connector and a second connector, wherein the second connector of the first aseptic coupling device can be received within the first connector of the second aseptic coupling device and wherein the second connector of the second aseptic coupling device can be received within the first connector of the first aseptic coupling device.

13. The aseptic coupling arrangement of claim 12, wherein the first and second connectors of the first and second aseptic coupling devices are configured to align the front faces of each main body such that the front faces are parallel to each other.

14. The aseptic coupling arrangement of claim 8, wherein the first and second aseptic coupling devices have substantially similar constructions.

15. The aseptic coupling arrangement of claim 14, wherein the first and second aseptic coupling devices have identical constructions.

16. The aseptic coupling arrangement of claim 8, wherein the first and second aseptic coupling devices are each provided with a visual indicator that is visible when the first and second aseptic coupling devices are in an uncoupled state, and that is obscured from view when the first and second aseptic coupling devices are in a coupled state.

17. The aseptic coupling arrangement of claim 16, wherein the visual indicator is set back from a rear face of the main body of each of the first and second aseptic coupling devices.

18. The aseptic coupling arrangement of claim 8, wherein the first aseptic coupling device further comprises a first sealing member received at least partially within the first main body, and wherein the second aseptic coupling device further comprises a second sealing member received at least partially within the second main body.

19. The aseptic coupling arrangement of claim 18, wherein while the first protective cover is in the closed position the first protective cover compresses the first sealing member, and wherein while the second protective cover is in the closed position the second protective cover compresses the second sealing member.

20. The aseptic coupling arrangement of claim 18, wherein while: (i) the first and second aseptic coupling devices are coupled together and (ii) the first and second protective covers are separated from the first and second main bodies respectively, the first and second sealing members contact each other to form a seal.

21. The aseptic coupling arrangement of claim 8, wherein removal of the first protective cover away from the first main body causes the first membrane to be removed from the first front face, and wherein removal of the second protective cover away from the second main body causes the second membrane to be removed from the second front face.

22. The aseptic coupling arrangement of claim 8, wherein the first protective cover is rotatable about a first hinge member between the closed position and the open position, and wherein the second protective cover is rotatable about a second hinge member between the closed position and the open position.

* * * * *